(12) United States Patent
Chakravarthy et al.

(10) Patent No.: US 10,321,823 B2
(45) Date of Patent: Jun. 18, 2019

(54) SYSTEM AND METHOD TO FLAG ARRHYTHMIA EPISODES FOR URGENT REVIEW

(71) Applicant: Medtronic Monitoring, Inc., San Jose, CA (US)

(72) Inventors: Niranjan Chakravarthy, Eden Prairie, MN (US); Abhi Chavan, Maple Grove, MN (US); Brion Finlay, Brooklyn Park, MN (US)

(73) Assignee: Medtronic Monitoring, Inc.

( * ) Notice: Subject to any disclaimer, the term of this patent is extended or adjusted under 35 U.S.C. 154(b) by 362 days.

(21) Appl. No.: 14/976,667

(22) Filed: Dec. 21, 2015

(65) Prior Publication Data

US 2017/0172413 A1 Jun. 22, 2017

(51) Int. Cl.
*A61B 5/00* (2006.01)
*A61B 5/0452* (2006.01)
(Continued)

(52) U.S. Cl.
CPC .......... *A61B 5/0006* (2013.01); *A61B 5/0205* (2013.01); *A61B 5/046* (2013.01); *A61B 5/0408* (2013.01); *A61B 5/04012* (2013.01); *A61B 5/0452* (2013.01); *A61B 5/0464* (2013.01); *A61B 5/0468* (2013.01); *A61B 5/0472* (2013.01); *A61B 5/6833* (2013.01); *A61B 5/053* (2013.01); *A61B 5/08* (2013.01); *A61B 5/1116* (2013.01); *A61B 5/1118* (2013.01)

(58) Field of Classification Search
CPC . A61B 5/0006; A61B 5/0205; A61B 5/04012; A61B 5/0452; A61B 5/046–0472
See application file for complete search history.

(56) References Cited

U.S. PATENT DOCUMENTS

| 4,589,420 A | 5/1986 | Adams et al. |
| 6,454,708 B1* | 9/2002 | Ferguson ............ A61B 5/0022 128/903 |

(Continued)

FOREIGN PATENT DOCUMENTS

| WO | 2009112976 A1 | 9/2009 |
| WO | 2015002945 A2 | 1/2015 |

OTHER PUBLICATIONS

Baman, "Relationship between burden of premature ventricular complexes and left ventricular function", Heart Rhythm, vol. 7, 2010, 865-869.

(Continued)

*Primary Examiner* — Scott M. Getzow
(74) *Attorney, Agent, or Firm* — Billion & Armitage; Michael A. Collins

(57) ABSTRACT

A system and method of flagging monitored ECG samples for urgent review by a human expert is described, and includes monitoring an electro-cardiogram (ECG) signal of the patient with an adherent device that includes a plurality of electrodes. Based on the monitored ECG signal, detected rhythm abnormalities in the patient are detected and ECG samples are collected with respect to detected rhythm abnormalities. One or more features are identified with respect to each ECG sample, and the features are utilized to flag ECG samples for urgent review by a human expert.

11 Claims, 4 Drawing Sheets

(51) Int. Cl.

| | |
|---|---|
| *A61B 5/0408* | (2006.01) |
| *A61B 5/0205* | (2006.01) |
| *A61B 5/046* | (2006.01) |
| *A61B 5/0464* | (2006.01) |
| *A61B 5/04* | (2006.01) |
| *A61B 5/0468* | (2006.01) |
| *A61B 5/0472* | (2006.01) |
| *A61B 5/053* | (2006.01) |
| *A61B 5/08* | (2006.01) |
| *A61B 5/11* | (2006.01) |

(56) References Cited

U.S. PATENT DOCUMENTS

| | | | |
|---|---|---|---|
| 7,181,282 B1 | 2/2007 | Province et al. | |
| 7,715,906 B2 | 5/2010 | Krause et al. | |
| 8,483,813 B2 | 7/2013 | Zhang et al. | |
| 9,107,571 B2 | 8/2015 | Strauss et al. | |
| 2009/0062671 A1* | 3/2009 | Brockway | A61B 5/0031 600/518 |
| 2012/0232416 A1 | 9/2012 | Gilham et al. | |
| 2013/0274584 A1 | 10/2013 | Finaly et al. | |
| 2016/0274162 A1* | 9/2016 | Freeman | G01R 31/02 |

OTHER PUBLICATIONS

Cha, et al., "Premature Ventricular Contraction-Induced Cardiomyopathy A Treatable Condition", Circ Arrhythm Electrophysiol, 5, 2012, 229-236.

Garcia, et al., "Arrhythmia Recognition, The Art of Interpretation", Jones & Bartlett Learning, First Edition, Nov. 12, 2003, 633 pages.

Hasdemir, et al., "Tachycardia-induced cardiomyopathy in patients with idiopathic ventricular arrhythmias: the incidence, clinical and electrophysiologic characteristics, and the predictors", J Cardiovasc Electrophysiol, vol. 22, 2011, 663-668.

Kanei, et al., "Frequent premature ventricular complexes originating from the right ventricular outflow tract are associated with left ventricular dysfunction", Annals of Noninvasive Electrocardiology, vol. 13, 2008, 81-85.

Niwano, et al., "Prognostic significance of frequent premature ventricular contractions originating from the ventricular outflow tract in patients with normal left ventricular function", Heart, vol. 95, 2009, 1230-1237.

Notification of Transmittal of the International Search Report and the Written Opinion of the International Searching Authority, or the Declaration for PCT Application No. PCT/US2016/065302, dated Mar. 28, 2017.

* cited by examiner

US 10,321,823 B2

SYSTEM AND METHOD TO FLAG ARRHYTHMIA EPISODES FOR URGENT REVIEW

TECHNICAL FIELD

The present disclosure is related in general to patient monitoring and in particular to monitoring and detecting arrhythmia episodes that may require urgent care.

BACKGROUND

A benefit of wearable devices capable of monitoring electrocardiogram (ECG) signals of a patient for extended periods of time is the ability to collect large amounts of patient data. Typically, data collected by wearable devices is transmitted to a remote monitoring center for analysis, including review by a human expert to verify diagnosis. However, this review of collected ECG data is done in a first-in, first out basis, such that ECG data is reviewed in the order it is collected. As a result, ECG data indicative of an urgent condition is detected only during the normal course of review. For conditions such as ventricular tachycardia (VT), ventricular fibrillation (VF), very high rate tachycardia, very low rate bradycardia, and/or long pauses, an urgent response may improve the outcome for the patient and is therefore desirable.

Therefore, it would be beneficial to provide a system and method of filtering the large amounts of patient data collected by extended wear adherent patches to provide a human expert with samples indicative of potentially urgent conditions.

SUMMARY

According to an exemplary embodiment, a method of flagging monitored ECG samples for urgent review by a human expert includes monitoring an electrocardiogram (ECG) signal of the patient with an adherent device that includes a plurality of electrodes. The method further includes detecting a rhythm abnormality in the patient based on the monitored ECG signal and collecting ECG samples associated with the detected rhythm abnormality. Features are identified with respect to the ECG sample and utilized to flag ECG samples for urgent review, wherein the flagged ECG samples are communicated to a human expert for review/validation.

Another exemplary embodiment of the present invention includes a system for flagging monitored ECG samples for urgent review by a human expert. The system includes an adherent device that includes a plurality of electrodes and sensing circuitry for monitoring an electrocardiogram (ECG) signal of a patient to which the adherent device is affixed. The system further includes a processing module configured to receive the monitored ECG signal, wherein the processing module detects rhythm abnormalities in the patient based on the monitored ECG signal, collects an ECG sample associated with detected rhythm abnormalities, identifies one or more features associated with the ECG sample or monitored concurrently with collection of the ECG sample, and flags ECG samples for urgent review based on the one or more identified features, wherein flagged ECG samples are communicated to a human expert for review.

DETAILED DESCRIPTION

The present invention is related to a system and method of monitoring electrocardiogram signals from a patient and flagging/prioritizing received ECG samples for review by a human expert. In this way, rather than have the ECG samples reviewed in the order they are received at the remote monitoring center, the present invention prioritizes the ECG samples to ensure that those that present the greatest risk to the patient are reviewed first (i.e., those indicative of an arrhythmic episode). In this way, the present invention provides a system and method to review large amounts of ECG data collected by adherent devices (associated with a plurality of different patients) and identifies those ECG samples indicative of an abnormal condition that would benefit from urgent review by a human expert. Based on the review by the human expert, appropriate steps can be taken to provide treatment to the patient.

Figure 1:
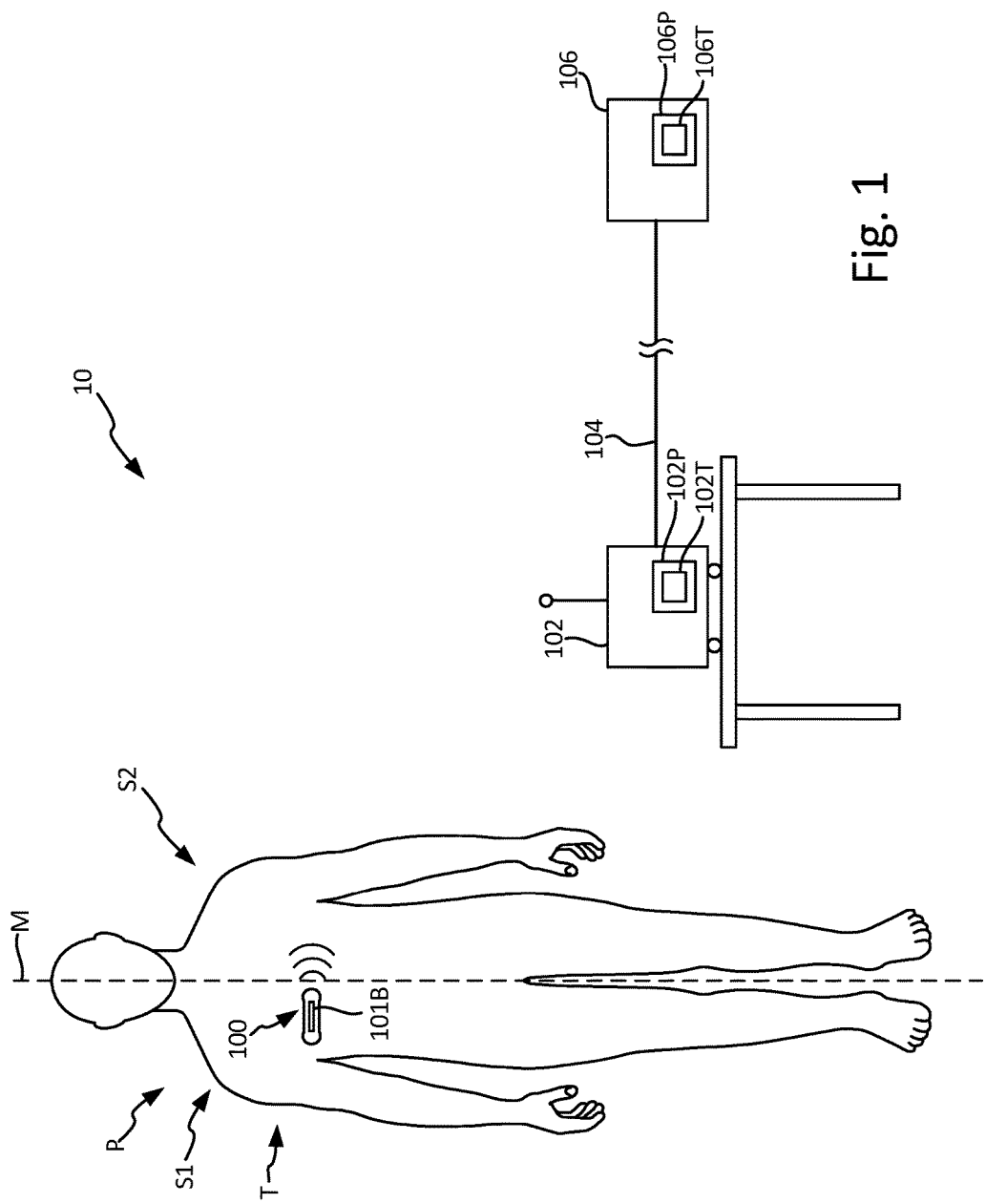
FIG. 1 illustrates a schematic view of a monitoring and treatment system comprising a patient utilizing a medical device capable of long-term monitoring of electrocardiogram (ECG) signals according to an embodiment of the present invention.

FIG. 1 shows a patient P and a monitoring system 10. Patient P comprises a midline M, a first side S1, for example a right side, and a second side S2, for example a left side. Monitoring system 10 comprises a patient measurement device 100, gateway 102, and remote monitoring center 106. In the embodiment shown in FIG. 1, patient measurement device 100 (hereinafter, "adherent device 100") is an adherent device that attaches to the skin of the patient, but in other embodiments may be an implantable or injectable device. Adherent device 100 can be adhered to a patient P at many locations, for example thorax T of patient P. In many embodiments, the adherent device may adhere to one side of the patient, from which side data can be collected. A benefit of utilizing an adherent device such as adherent device 100 is that it may be utilized to collect physiological data from the patient while the patient goes about normal day-to-day activities outside of a hospital setting. When rhythm abnormalities are detected, an ECG sample recorded by adherent device 100 can be stored and subsequently transmitted to remote monitoring center 106 for review by a human expert. In response to the received ECG samples, the human expert may verify the presence of an abnormal condition and take appropriate steps (e.g., provide instructions to the patient, physician, etc.). As described in more detail below, rather than review the ECG samples in the order they are received at remote monitoring center 106, the ECG samples are automatically reviewed and prioritized for subsequent review by the expert/technician. In this way, urgent conditions may be flagged for prioritize review over other ECG samples. However, when prioritizing one set of ECG samples over another, it is of the utmost importance that as many false positives are removed as possible to prevent ECG samples without any underlying condition being prioritized over other ECG samples.

Adherent device 100 is capable of monitoring a variety of different types of physiological parameters, including one or more of electro-cardiogram signals (ECG), bio-impedance, respiration, heart rate, heart rhythm, heart rate variability (HRV), heart rate turbulence (HRT), heart sounds, respiratory sounds, blood pressure, activity (e.g., rest, active), posture, and wake/sleep. In one embodiment, ECG signals are utilized to automatically detect abnormal heart rhythms such as tachycardia, bradycardia, pause, atrial fibrillation, ventricular tachycardia (VT) and ventricular fibrillation (VF). In one embodiment, detection of these conditions occurs locally on adherent device 100, wherein detected conditions result in the corresponding ECG signal being stored for subsequent analysis—either locally or at remote monitoring center 106. The collected ECG samples are communicated to remote monitoring center 106, which prioritizes the ECG samples according to an embodiment of the present invention. However, in other embodiments local processing of the ECG samples may be utilized to flag ECG samples that should receive a higher prioritization. In the latter embodiment, subsequent communication of the ECG sample to remote monitoring center 106 would include the prioritization flag indicating whether the ECG sample should receive priority.

Adherent device 100 can wirelessly communicate with remote center 106. The communication may occur directly (via a cellular or Wi-Fi network), or indirectly through intermediate device or gateway 102. As described above, in one embodiment ECG signals monitored by adherent device 100 are communicated in their entirety to remote center 106 for analysis. In other embodiments, adherent device 100 locally provides some level of analysis with respect to monitored ECG signals. For example, as described previously, in one embodiment adherent device 100 monitors ECG signals and through local processing detects rhythm abnormalities. The ECG sample associated with the detected abnormality is stored and communicated to remote center 106 for subsequent analysis and prioritization. In still other embodiments, only those ECG samples identified locally as requiring urgent review are communicated wirelessly to remote center 106. Other non-prioritized ECG samples may be communicated subsequently via traditional, wired connections.

The gateway 102 may comprise components of the zLink™, a small portable device similar to a cell phone that wirelessly transmits information received from adherent device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by human experts to verify accuracy. In the present invention, ECG samples collected/stored by remote center 106 from one or more adherent devices 100 are prioritized prior to being displayed or presented to a human expert for review and/or verification of detected conditions. Reports may then be generated at remote monitoring center 106 for communication to the patient's physician or care provider.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG samples—monitored by adherent device 100 may be analyzed by one or more of the distributed processors included as part of adherent device 100, gateway 102, and/or remote monitoring center 106.

In an exemplary embodiment, adherent device 100 may continuously monitor physiological parameters, communicate wirelessly with a remote center, and provide alerts when necessary. The adherent patch may attach to the patient's thorax and contains sensing electrodes, battery, memory, logic, and wireless communication capabilities. In an embodiment described in more detail with respect to FIG. 2, adherent device 100 collects physiological data from the patient that includes ECG data. In response to a detected rhythm abnormality, an ECG sample is collected for subsequent communication to remote monitoring center 106. The collected ECG samples may be analyzed locally or at remote monitoring center 106 in order to prioritize the ECG samples. Prioritized/flagged ECG samples are provided to the expert/technician ahead of non-prioritized ECG samples. In this way, ECG samples representing potentially urgent conditions are reviewed and assessed more quickly than other monitored ECG samples.

Figure 2:
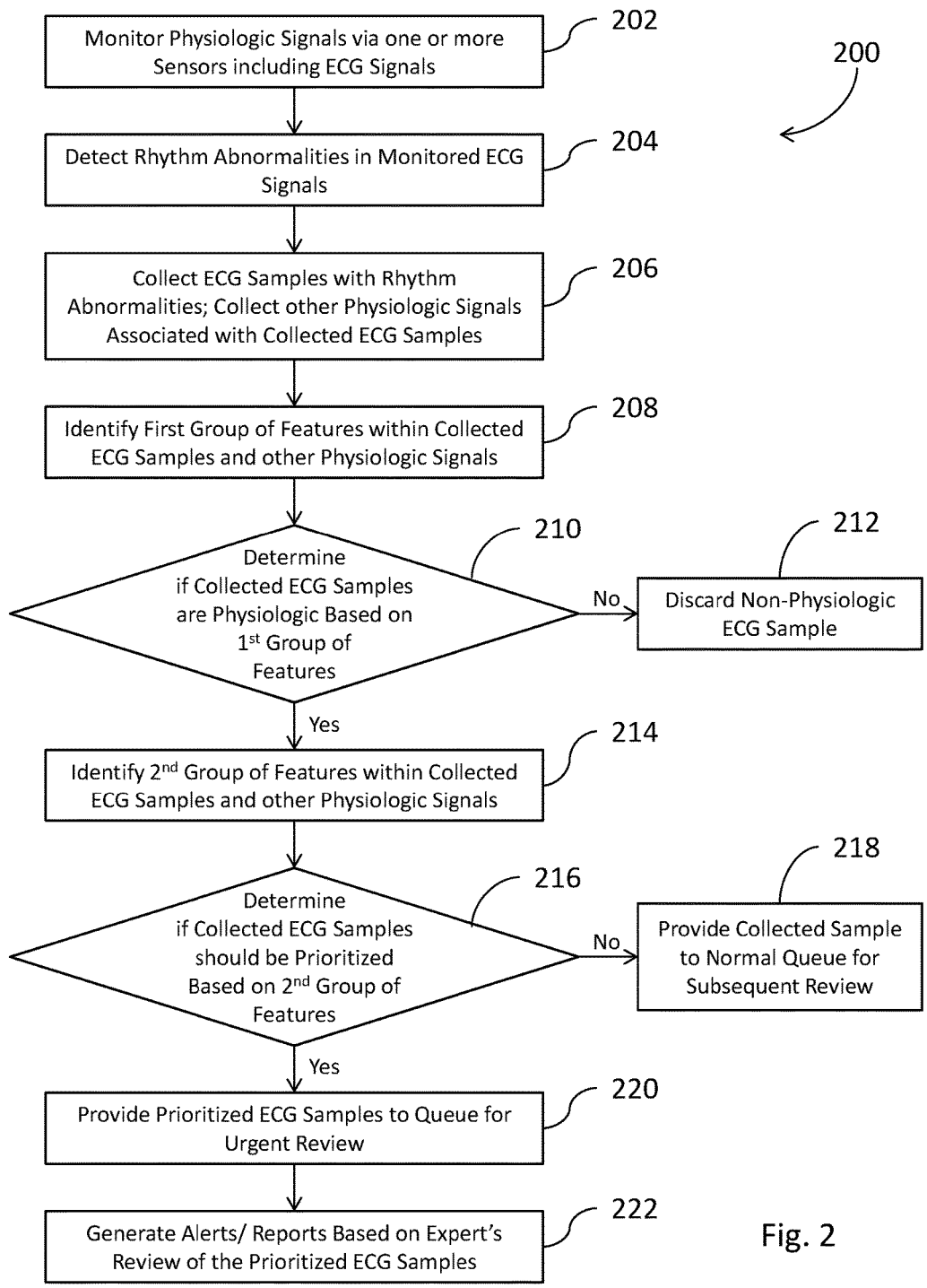
FIG. 2 is a flowchart that illustrates a method of discarding/prioritizing ECG samples for a human expert to review according to an embodiment of the present invention.

FIG. 2 is a flowchart 200 that illustrates a method of flagging/prioritizing ECG samples to be reviewed by a human expert according to an embodiment of the present invention.

At step 202, one or more physiological signals are monitored via the one or more sensors located on adherent device 100. As discussed above, physiological signals may include electrocardiogram (ECG) signals, bioimpedance measurements, respiration measurements, body posture measurements, and activity level measurements. In addition to physiological signals, one or more other signals may be monitored at step 202, including signals such as detachment status.

At step 204, the monitored ECG signal is utilized detect rhythm abnormalities associated with a patient. In one embodiment, rhythm abnormalities are detected locally on adherent device 100. In other embodiments, ECG signals monitored by adherent device 100 are communicated to remote monitoring system 106 for review and detection of rhythm abnormalities. However, the latter method requires a significant amount of information (e.g., all monitored ECG data) to be communicated to remote monitoring center 106. In contrast, by detecting rhythm abnormalities locally on adherent device 100, only those ECG samples associated with the detected abnormalities need to be communicated to remote monitoring center 106. In addition to the ECG samples, other data obtained from the monitored ECG signal, such as heart rate, flagged arrhythmic beats, number of arrhythmic beats, number of normal beats, ECG statistics, etc., may be communicated to remote monitoring center 106 along with the selected ECG samples. Furthermore, additional data collected by adherent device 100 (both physiological and non-physiological) may be communicated to remote monitoring center 106. For example, this may include activity level of the patient (resting, moving), status of the adherent device (e.g., attached) as well as other information that may be useful in analyzing the patient's condition. In one embodiment, rhythm abnormalities may include one or more of tachycardia, bradycardia, pause, atrial fibrillation, ventricular tachycardia/ventricular fibrillation.

At step 206, for each abnormality detected, an ECG sample is collected and/or stored. The size/duration of the ECG sample may be predetermined as a window centered around the detected abnormality, or may be selected based on the type/duration of the abnormality itself. For example, an ECG sample may consist of a small window centered on the detected irregular beat, or may consist of a plurality of beats collected with respect to an sample (e.g., forty beats associated with a tachycardia sample). Collection of an ECG sample may also include annotating or otherwise providing some additional information with respect to the collected sample. For example, in one embodiment, for a detected VT/VF abnormality, the collected ECG sample may comprise a number of beats, some of which are arrhythmic and other which are not. Collection of the ECG sample may include flagging those beats identified as arrhythmic. As discussed in more detail below, in subsequent steps this allows a feature to be identified within the collected ECG sample that determines the number of arrhythmic events versus the number of normal beats. In other embodiments, however, flags identifying arrhythmic beats may be established at remote monitoring center 106.

In addition to ECG samples, one or more other physiological signals associated with the collected ECG samples may be collected and associated with the collected ECG sample. For example, physiological signals including one or more of bioimpedance signals, respiration signals, activity level signals, and the like may be collected and associated with the collected ECG sample. As discussed in more detail below, these other physiological signals may be utilized to assess the veracity of the monitored ECG signal.

In one embodiment, the collected data—including the collected ECG data as well as the physiological data associated with the collected ECG data—are communicated to remote monitoring center 106. In one embodiment, ECG samples are communicated shortly after being collected. However, in other embodiments communication with remote monitoring station may be intermittent and/or expensive, in which case ECG samples may be communicated in a batch to remote monitoring center 106. In addition to ECG samples, other data collected by the adherent devices, such as signals indicating whether the adherent device is attached, measured heart rate, bio-impedance, respiration, activity level, etc., may be communicated to remote monitoring center. As described above, data collected outside of the monitored ECG signal may include both physiological and non-physiological data. In other embodiments, one or more the steps discussed below may be implemented on the adherent device. For example, as discussed with respect to steps 208 and 210, for those ECG signals being discarded, it may be beneficial to make the determination of whether to discard the ECG signal prior to incurring the cost of communicating the ECG signal to the remote monitoring center.

At step 208, a first group of features are automatically identified within the collected physiological data associated with the collected ECG samples. For example, as shown in the embodiment illustrated in FIG. 3, the first group of features may be identified from the collected physiological signals collected apart from the monitored ECG signal. The purpose of the first group of features is to assess—not whether the collected ECG sample should be tagged for urgent review—but whether the collected ECG signal needs to be reviewed at all. In instances in which the collected physiological signals indicate a clearly non-physiological source of the ECG signal (e.g., the adherent device is not attached to the patient), then the collected ECG signal should be "discarded". The term "discard" does not imply that these ECG samples are permanently deleted or otherwise not available for subsequent review. Rather, the term "discard" is utilized to indicate a status of these ECG samples as not containing relevant physiological data. Discarded ECG samples are not queued for subsequent review. A benefit of this approach is that the discarded ECG signal does not incur the expense of subsequent analysis.

The first group of features may be derived from one or more of the physiological signals monitored by adherent device 100, including one or more of a bio-impedance signal, respiration signal, body posture signal (derived from an accelerometer, for example), activity level signal, and/or a detachment status level.

More particularly, in one embodiment the bio-impedance signal is monitored for a change in bio-impedance, wherein a sudden change in the monitored bio-impedance is indicative of the adherent device being removed from the patient. In another embodiment, the first group of features may include a respiration signal, which in one embodiment is a frequency space representation of the bioimpedance signal that is utilized to detect a non-physiological signal. In another embodiment, body posture (as determined from an accelerometer) is utilized to detect a non-physiological signal. For example, an accelerometer that registers absolutely no movements over a period of time may indicate that the adherent device is sitting on a table, rather than attached to a patient. In another embodiment, a detachment signal may be utilized to detect that the adherent device is not connected to the patient, and therefore that any signals measured are non-physiologic.

At step 210, the first group of features is utilized to determine the collected ECG signal is non-physiological in nature, and therefore should be discarded. For example, a collected ECG sample may be discarded in response to a determination that the adherent device was detached at the time of collection. This indicates that the collected ECG sample is non-physiological (i.e., not related to monitoring of the patient), and therefore irrelevant to further analysis. In other embodiments, alone or in combination, additional features or combinations of features including bioimpedance, respiration, body posture, and/or activity level may be similarly utilized to discard ECG samples that do not contain physiologically relevant data. For example, bio-impedance signals—and in particular large changes in the bio-impedance signal from previous measurements—may be utilized to detect a noise indicating that the monitored ECG sample is noisy and/or non-physiological. In another embodiment, respiration measurements derived from the bio-impedance signal may also be utilized to determine whether the ECG sample is non-physiological. In another embodiment, signals received from an accelerometer are utilized to determine body posture, which in turn are utilized to detect whether received signals are non-physiological. In another embodiment, signals received from the accelerometer are utilized to monitor activity level of the patient. Once again, the measured activity level can be utilized to determine whether the signals monitored by the device are non-physiological. For example, if the activity level is too high or too low, the monitored signal is non-physiological, indicating that the device is either not attached to the patient or is very noisy.

ECG samples determined at step 210 to be non-physiological in nature are discarded at step 212. As described above, discarding an ECG signal does not necessarily mean delete. Rather, "discard" means that the ECG sample is not stored for review by an expert, but may be retained for subsequent analysis and/or troubleshooting.

ECG samples determined at step 210 to be directed to a physiological signal are provided for subsequent review and analysis at step 214 to identify a second group of features associated with the ECG sample (as well as other physiological signals that may be utilized). For example, in one embodiment an identified feature includes a ratio of VT/VF beats to total beats in an sample. In embodiments in which for an ECG sample, flags are set identifying arrhythmic beats versus normal beats, the VT/VF beats to total beats ratio may be calculated based on a simple count of the number of flags set versus the total number of beats. In other embodiments, part of the analysis performed at step 208 is to identify those beats that are arrhythmic and determine the count of arrhythmic beats to normal beats. Additional features that may be identified include ratio of noise beats to total beats in an sample, ECG statistics (e.g., maximum, minimum, histogram distribution, etc.), beat/heart-rate and variability statistics (e.g., mean, standard deviation, etc.), as well as others. In addition, first features identified at step 208 may be retained for use in subsequent steps. In some embodiments, first features may be further analyzed to provide a second feature. For example, in one embodiment a sudden change in bio-impedance was monitored at step 208 in order to detect a non-physiological status of the ECG sample. At step 214, the bio-impedance value may be further analyzed to derive another feature, such as hydration, that may be used in subsequent steps to assess whether the ECG sample should be prioritized.

A benefit of identifying a first set of features at step 208 is that for those ECG samples that are discarded, no further analysis of the ECG samples (or other monitored physiological signals) is required at step 214, thus conserving resources. In addition, in some embodiments the first features identified at step 208 may be identified locally on adherent device 100. A benefit of this approach is that only ECG samples (and other monitored physiological signals) that are determined to be physiological in nature are communicated to a remote monitoring center for subsequent review. This similarly conserves resources by reducing the number of ECG samples communicated to the remote monitoring center. It should be noted that in other embodiments, all ECG samples collected that exhibit rhythm abnormalities—or indicated by the patient to indicated rhythm abnormalities—are communicated to remote monitoring center for subsequent review via steps 208-222.

Figure 4:
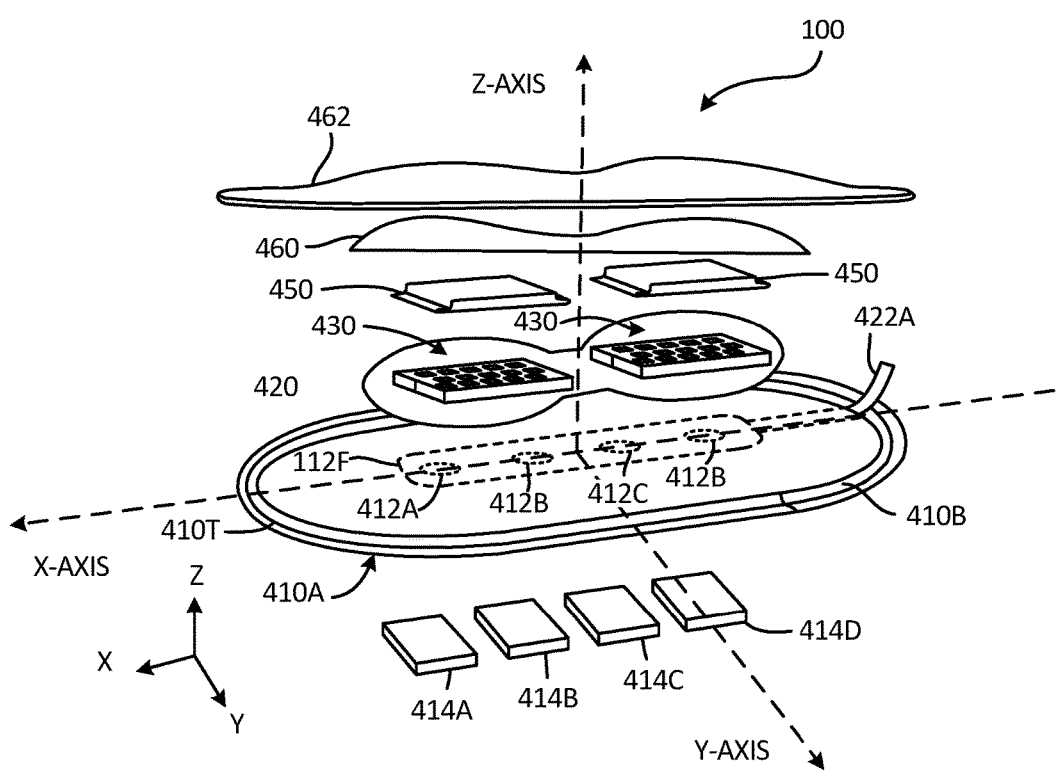
FIG. 4 shows an exploded view of an adherent device according to an embodiment of the present invention.

At step 216, the identified features are used to flag ECG samples that require urgent review by the human expert. Various combinations of identified features may be utilized to flag those samples that require urgent review, an example of which is shown in FIG. 4 to detect a VT/VF condition that requires urgent review. Identified features may be utilized not only to detect the presence of an abnormal condition that requires urgent review, but also to ensure that noisy artifacts do not result in an ECG sample being inadvertently flagged for urgent review without an underlying abnormal condition. That is, the present invention seeks to identify samples that should be flagged as urgent, while preventing/minimizing incorrectly flagged samples, so as to reduce false alarms being prioritized for review. If at step 216 it is determined that the collected ECG samples should not be flagged for prioritized review, then at step 218 the collected ECG samples are provided to the normal queue for subsequent review by a human expert or technician. In this way, the collected ECG samples are still reviewed, but are not given prioritized or urgent review.

If at step 216 it is determined that the ECG sample should be prioritized for urgent review based on the second group of features, then at step 220 the flagged/prioritized ECG samples are provided to a human expert for review. In this way, rather than review ECG samples in a first-in, first out type queue, the claimed invention allows those flagged/prioritized ECG samples to be reviewed first (i.e., out-of-order). In some embodiments, different levels of prioritization may be assigned within the framework of flagged/prioritized ECG samples. In other embodiments, flagging an ECG sample is a binary determination, in which case flagged ECG samples are reviewed in the order they are received. Regardless of whether various prioritization levels are assigned the ECG samples, or whether the flagged status is binary, the present invention allows the human expert to review ECG samples identified as urgent prior to other ECG samples.

At step 222, alerts and/or reports are generated based on the expert's review of the sample. In embodiments in which the expert confirms that the sample flagged at step 216 indicates an urgent condition, the expert may generate an alert provided to the patient or physician indicating the urgent condition. If the expert determines that the sample was flagged incorrectly, or otherwise does not represent an urgent condition, then the expert may either return it to the queue of non-prioritized ECG samples to be reviewed, or may generate a report indicating the incorrectly flagged ECG sample. In the instance in which the expert's review of the ECG sample indicates an urgent condition, a communication may be sent to the patient that includes instructions (e.g., go to hospital, taken medication, etc.). In addition, a communication may be sent to the patient's physician to allow the physician to provide instructions to the patient as required, or to emergency personnel with instructions on the location of the patient and treatment required.

Figure 3:
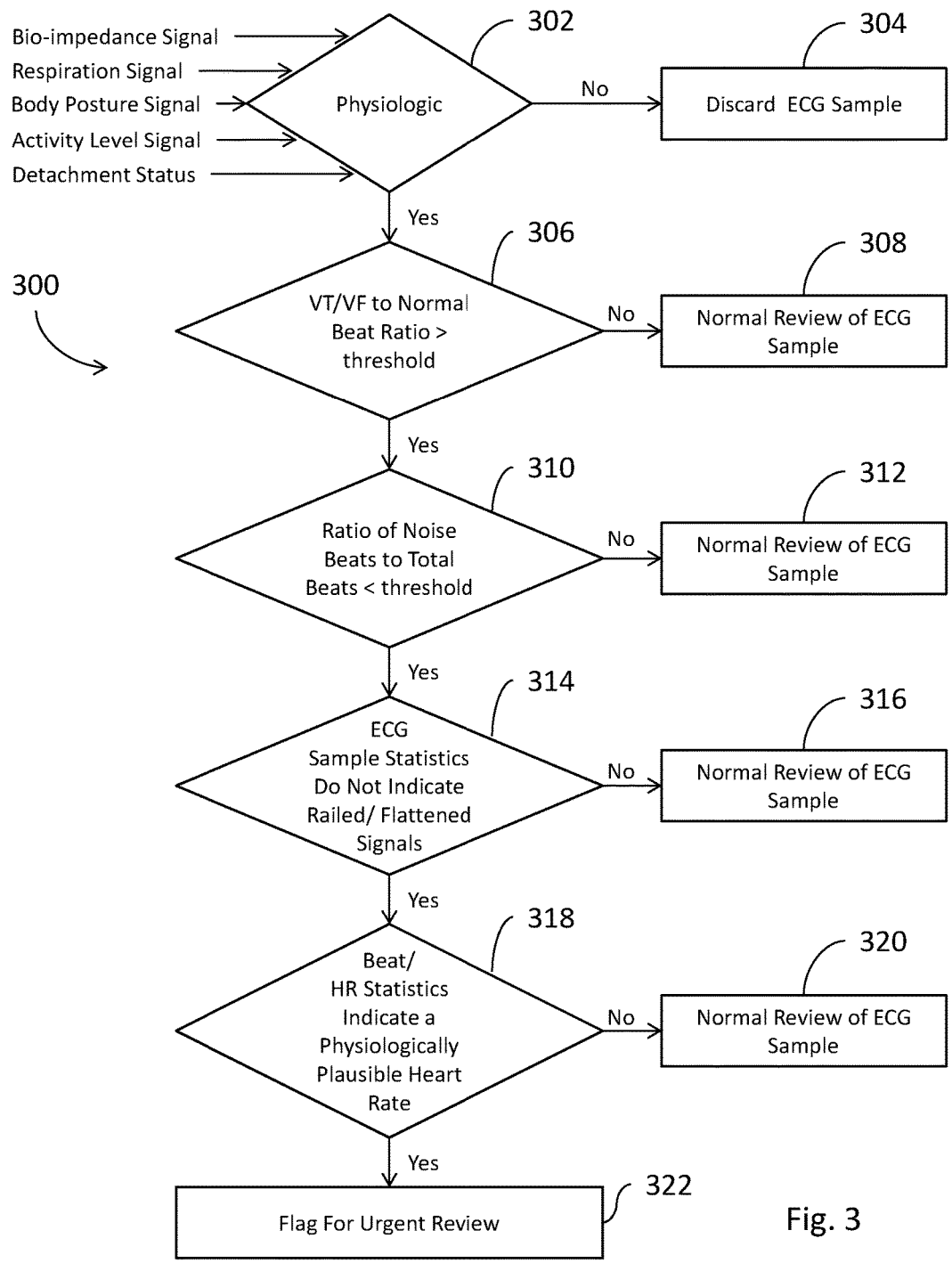
FIG. 3 is a flowchart that illustrates in more detail utilization of identified features to flag ECG samples that should be discarded/prioritized for urgent review by a human expert according to an embodiment of the present invention.

FIG. 3 is a flowchart 300 that illustrates in more detail utilization of identified features to flag samples that should be prioritized for urgent review by an expert/technician according to an embodiment of the present invention. The embodiment shown in FIG. 3 describes flagging ECG samples related to a particular type of abnormal rhythm known as ventricular tachycardia/ventricular fibrillation (VT/VF). In other embodiments, other features and combinations of features may be utilized. In addition, other types of rhythm abnormalities may be detected and flagged for urgent review.

At step 302, a first plurality of features is utilized to determine whether a monitored ECG sample is physiologic. In the embodiment shown in FIG. 3, the first plurality of features is selected from a group consisting of a bio-impedance signal, a respiration signal, a body posture signal, an activity level signal, and a detachment status signal. If the first plurality of signals indicates that the monitored ECG signal is non-physiological, then at step 304 the ECG sample is discarded. If the first plurality of signals indicates that the monitored ECG signal is physiological, then at step 306 analysis of the ECG sample continues.

In the embodiment shown in FIG. 3, at step 306 a ratio of VT/VF beats to normal beats is compared to a threshold to determine whether the ECG sample indicates a presence of VT/VF. In one embodiment, the ratio of VT/VF beats to normal beats is determined at remote monitoring center via analysis of the ECG sample. This may include identification of VT/VF beats as well as identification of normal beats, wherein once identified the respective beats are counted and utilized to determine the desired ratio. In other embodiments, the ECG sample being analyzed may have been previously flagged to identify VT/VF beats and normal beats, respectively. In this case, determination of the ratio of VT/VF beats to normal beats only requires counting the respective flags and calculating the ratio.

The threshold may be static or dynamic. For example, a static threshold may be selected to be applied across all patients, and may be based on historical data collected that indicates the threshold ratio at which VT/VF becomes an urgent issue, or may be selected based on a level that indicates the likely presence of VT/VF. In one embodiment, the threshold is defined as requiring at least 5% of detected beats to be VT/VF beats (i.e., more than one VT/VF beat for every two-hundred normal beats), although in other embodiments the threshold may be modified. A dynamic threshold value may be selectively defined by some criteria, such as age, race, activity-level, etc., of the patient. This allows different thresholds to be selected based different patient profiles. In addition, the threshold utilized at step 306 may be different than the threshold or value utilized by the adherent device 100 to identify the ECG sample as indicative of a rhythm abnormality such as VT/VF—which results in collection of the ECG sample for subsequent review. For example, an adherent device may collect an ECG sample in response to detection of consecutive VT/VF beats, a number of VT/VF beats within a defined time period, or some other criteria indicating the possibility that a VT/VF condition is present.

If the ratio of VT/VF beats to normal beats does not exceed the defined threshold, then at step 308 a determination is made that the ECG sample does not need to be flagged for urgent review and the process ends. Those ECG samples for which it is determined that no urgent review is required, the ECG sample is returned to the normal queue (stack) of ECG samples to be reviewed by an expert/technician at a later time (i.e., non-prioritized). In some embodiments, a report may be generated indicating the results of the analysis and ultimate determination that urgent/prioritized review is not required. In other embodiments, because ultimately the ECG sample was not flagged for urgent review, no report is generated until the ECG sample is reviewed in the normal course of review by a human expert.

If at step 306 it is determined that the ratio of VT/VF beats to normal beats exceeds the defined threshold, then review continues of other identified features at step 310. In the embodiment shown in FIG. 3, step 310 reviews the ECG sample for excessive noise (e.g., noisy beats). An ECG sample comprised of a high threshold of noisy beats typically indicates a bad connection, presence of interference, or other electrical issue that results in distortion of the underlying ECG signal. While the presence of noise does not preclude the presence of an abnormal heart rhythm, it does make it much more likely than the initial detection of a rhythm abnormality by the adherent device was a result of the noisy beats, and not an underlying VF/VT condition. To prevent ECG samples from being flagged for urgent/prioritized review that include a large noise component, the embodiment shown in FIG. 3 utilizes a feature associated with identification of noisy beats to prevent these samples from being flagged for urgent review.

In particular, at step 310 the ratio of noisy beats to total beats is compared to a threshold value. If the ratio of noise beats to total beats is greater than the threshold value (indicating a noisy ECG sample), then the ECG sample is not flagged for urgent review as indicated at step 312 and reports are generated (or not generate) as discussed with respect to step 308. If the ratio of noise beats to total beats is less than a threshold value, then the method continues at step 314.

As described with respect to identification of VT/VF beats, identification of noise beats may be performed locally by the adherent device, or may be done by resources at the remote monitoring center. Once identified, the respective noise beats and normal beats within an ECG sample are counted in order to calculate the ratio of noise beats to normal beats. In addition, the selected threshold may once again be static or dynamic. In embodiments in which the threshold is static, it may be selected based on historical data that indicates when the presence of noise becomes substantial enough to indicate a high likelihood that the initial detection of rhythm abnormalities was likely caused by the presence of noisy beats. For example, in one embodiment the threshold is set at 3%, meaning that out of one thousand normal beats, up to three may be noisy. In embodiments in which the threshold is dynamic, additional features such as age, race, activity level, etc. of the patient may be utilized to determine an appropriate threshold. In other embodiments, other measures of noise may be utilized other than ratio of noise beats to normal beats. For example, a measure of baseline noise in the ECG sample may be utilized.

If at step 310 it is determined that the adherent device is attached to the patient, then review of identified features continues at step 314. In the embodiment shown in FIG. 3, the next identified feature to be reviewed are ECG sample statistics, which provide a different type of noise metric utilized to detect false positives corresponding to railed/flatlined signals. Examples of the statistics that may be utilized include the maximum, minimum, and histogram distribution of the ECG sample. In this embodiment, the maximum describes the maximum amplitude of the monitored ECG signal, the minimum describes the minimum amplitude of the monitored ECG signal, and the histogram distribution describes the distribution of maximum/minimum values for each beat. For example, a non-noisy signal should display relatively low variability in the ECG samples (e.g., more than 90% of samples fall within an allowed range). If the monitored ECG sample exhibits a higher variability in the monitored ECG signal, then it is likely due to artifacts or noise associated with the signal. If the ECG sample statistics indicate a variability indicative of artifacts/noise, then a determination is made that the ECG sample should not be flagged for urgent review as indicated by step 316.

If the ECG sample statistics indicate a variability that is not indicative artifacts/noise, then review of the identified features continues at step 318. In the embodiment shown in FIG. 3, at step 318 the next identified feature reviewed is related to beat/HR statistics, to determine if the beats associated with the ECG sample or a sub-segment of the ECG sample present a physiologically plausible heart rate and heart rate variability. For example, in one embodiment, a physiologically plausible heart rate requires the heart rate to be within a range of 20 beats-per-minute (BPM) and 300 BPM. A detected heart rate outside of this range is determined to be the result of artifacts or noise. As a result, a determination is made that no urgent review is required as indicated at step 320. In addition to heart rate, other beat statistics may be utilized to determine whether the ECG sample being examined provides a physiologically plausible heart rate.

If at step 318, it is determined based on the beat and/or heart rate statistics that the ECG sample represents a physiologically plausible heart rate, then at step 322 the ECG sample is flagged for urgent review. Once flagged for urgent review, the ECG sample is put into a prioritized queue for review by a human expert. In addition to simply flagging the ECG sample, at step 322 the reason for the flagging may be identified (e.g., VT/VF sample), which may be utilized in further determining the prioritization status to be assigned to the ECG sample. For example, some conditions may provide a higher level of urgency than others, and therefore should be granted a higher level of prioritization. In addition, within the same condition, the seriousness of the various features identified may be utilized to assign various levels of prioritization to the ECG sample. For example, if the ratio of VT/VF beats to normal beats is higher than a second threshold (greater than the first threshold), then the ECG sample may be assigned a higher level of prioritization than if the ratio of VT/VF beats to normal beats is higher than a first threshold.

In addition, the order in which identified features are reviewed may be varied as necessary. In particular, a cost-benefit analysis may be utilized to determine the order in which features should be reviewed. For example, if a comparison of the VT/VF beats to normal beats ratio eliminates most of the ECG samples being reviewed from subsequent analysis, then it may be advantageous to analyze this feature first prior to review of other features. In this way, most ECG samples are filtered with respect to the first feature and no subsequent review is required, thereby conserving resources. Conversely, in other embodiments it may be beneficial to review those features that consume the least amount of resources first, regardless of how many ECG samples are likely to be filtered as a result. For example, determining whether the ECG sample is the result of a physiological signal—based on the first group of features—provides an advantageous method of filtering ECG samples to minimize the analysis required. However, it should be noted that in other embodiments the first group of features described with respect to step 302 may be analyzed subsequent to second features described with respect to steps 306-318, if beneficial. Therefore, it should be understood that in other embodiments, other combinations of features may be utilized, and the order in which the features are reviewed may be modified.

Although the embodiment shown in FIG. 3 analyzes the plurality of features in a sequential order, in other embodiments the plurality of features analyzed may be reviewed concurrently with one another. In addition, rather than determine that no urgent review is required in response to a single failed test, in other embodiments the result of each test may be weighted and an ECG sample may be flagged for urgent review despite one of the features returning a negative result. For example, if all features identified in FIG. 3 indicate a VT/VF condition that requires urgent review, but the ratio of noise beats to total beats is slightly greater than the threshold, the weighted combination of the other features may be substantial enough to initiate urgent review of the ECG sample.

In this way, the present invention reviews ECG samples indicative of rhythm abnormalities and based on one or more features identifies those samples that should be flagged for urgent review.

FIG. 4 is an exploded view, respectively, of embodiments of adherent device 100 utilized to identify abnormal rhythms and collect ECG samples associated with the detected abnormal rhythms. In some embodiments, adherent device 100 may also analyze one or more identified features collected from adherent device 100 to flag samples for urgent review.

In the embodiment shown in FIG. 4, adherent device includes adherent tape 410T, electrodes 412A, 412B, 412C, 412D with gels 414A, 414B, 414C, 414D, printed circuit board (PCB) 420, flexible connected 422A, electrical components/sensors 430 mounted on PCB 420, batteries 450, electronics housing cover 460, and flexible cover 462.

Adherent device 100 comprises at least two electrodes—although the embodiment shown in FIG. 8 includes electrodes 412A, 412B, 412C and 412D. Adherent device 100 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 100 comprises a first side, or a lower side 410A, that is oriented toward the skin of the patient when placed on the patient. The adherent patch 100 may also comprise a tape 410T which is a material, preferably breathable, with an adhesive (not shown) to adhere to patient P. Electrodes 412A, 412B, 412C and 412D are affixed to adherent patch 100. In many embodiments, at least four electrodes are attached to the patch. Gels 414A, 414B, 414C and 414D can each be positioned over electrodes 412A, 412B, 412C and 412D, respectively, to provide electrical conductivity between the electrodes and the skin of the patient. Adherent patch 100 also comprises a second side, or upper side 410B. In many embodiments, electrodes 412A, 412B, 412C and 412D extend from lower side 410A through adherent patch 100 to upper side 410B. An adhesive can be applied to upper side 410B to adhere structures, for example a breathable cover, to the patch such that the patch can support the electronics and other structures when the patch is adhered to the patient. In many embodiments, adherent patch 100 may comprise a layer of breathable tape 410T, for example a tricot-knit polyester fabric, to allow moisture vapor and air to circulate to and from the skin of the patient through the tape. Electrical signals received at electrodes 412A-412D may be communicated to electronic components 430 via flexible connection 422A, which is connected to a PCB (not shown). Cover 460 is positioned over batteries 450 and electronic components 430 to provide protection for both. In addition, flexible cover 462 is positioned to encase the flexible PCB 420, electronics components 430, and/or adherent patch 410 so as to protect at least the electronics components and the PCB In addition, electronic components 430 may include ECG circuitry utilized to generate electrocardiogram signals and data from two or more of electrodes 412A, 412B, 412C and 412D in many ways. In some embodiments, ECG circuitry (not shown) is connected to inner electrodes 412B and 412C, which may comprise sense electrodes of the impedance circuitry as described above. In many embodiments, the ECG circuitry may measure the ECG signal from electrodes 412A and 412D when current is not passed through electrodes 412A and 412D. In addition, electronic components 430 may include bioimpedance circuitry connected to two or more of electrodes 412A, 412B, 412C and 412D to allows electronic components 430 to measure a bioimpedance associated with the patient. In addition, electronic components 430 may include an accelerometer configured to measured motion of the patient.

In addition, electronic circuitry 430 may comprise a processor module that can be configured to analyze physiological parameters monitored by adherent device 100 and to control collection and transmission of data from the electrocardiogram circuitry. In one embodiment, the processor module included as part of electronic circuitry 430 comprises a tangible medium, for example read only memory (ROM), electrically erasable programmable read only memory (EEPROM) and/or random access memory (RAM). Processing of monitored physiological parameters such as ECG signals may therefore be distributed between the local processor module included as part of electronic circuitry 430 and remote monitoring system 106. For example, processing module may be configured to process monitored ECG signals to detect rhythm abnormalities in the monitored ECG signal. In addition, the processing module included as part of electronic circuitry 430 may collect and store ECG samples associated with detected rhythm abnormalities. The processing module may also collect features to be utilized in subsequent steps to determine whether to flag the ECG sample for urgent review. This may include analysis of the ECG sample itself to identify, for example, normal beats, noise beats, VT/VF beats, etc. In addition, this may include collection of features unrelated to the ECG sample, such as attachment status of the adherent device, bio-impedance measurements, posture, activity level, etc. of the patient. Although in some embodiments, the processing module flags ECG samples for urgent review, in other embodiments the collected ECG samples (and collected features) are communicated by electronic circuitry 430 to remote monitoring center 106.

In one embodiment, the processor module is configured to locally process bioimpedance data. For example, the bioimpedance signal monitored by the adherent device may be utilized to detect hydration levels of the patient, respiration of the patient, as well as features such as change in bioimpedance. In addition, the accelerometer signals received from the accelerometer may be utilized by the processor module to determine posture and/or activity level of the patient. As discussed above, however, in other embodiments calculations performed by the processor module may be provided remotely by the remote monitoring center.

In many embodiments, electronics components 430 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the electrocardiogram signal or other features collected by the adherent device 100. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

In this way, the disclosure provides a system and method of continuously monitoring ECG signals associated with a patient and identifying ECG samples associated with the patient that should be flagged for urgent review by an expert. In this way, the present invention provides a system and method for filtering through large amounts of ECG data generated as a result of long-term monitoring of patients (particularly for ambulatory patients not located in a hospital), but in a way that allows for identification of conditions that may require urgent action.

Discussion of Possible Embodiments

The following are non-exclusive descriptions of possible embodiments of the present invention.

A method of flagging monitored ECG samples for urgent review by a human expert may include monitoring an electro-cardiogram (ECG) signal of the patient with an adherent device that includes a plurality of electrodes and detecting a rhythm abnormality in the patient based on the monitored ECG signal. In addition, the method may include collecting an ECG sample associated with the detected rhythm abnormality. One or more features associated with the ECG sample and/or monitored concurrently with collection of the ECG sample are identified, and ECG samples are flagged for urgent review based on the one or more identified features. Flagged ECG samples are communicated to a human expert for review.

The method of the preceding paragraph can optionally include, additionally and/or alternatively any, one or more of the following features, configurations and/or additional components.

The method may further include discarding ECG samples from being reviewed for flagging for urgent review if it is determined from the one or more features that the ECG sample does not represent a physiological signal.

The method may further include wherein the step of identifying one or more features associated with the ECG sample or monitored concurrently with collection of the ECG sample further includes identifying a first group of features utilized to make determinations regarding whether the ECG sample represents a physiological signal and wherein the second group of features is utilized in the flagging step to determine whether the ECG sample should be flagged for urgent review, wherein a determination that the ECG sample does not represent a physiological signal results in the ECG sample being discarded.

The method may further include wherein the first group of features includes at least one of a bio-impedance signal, a respiration signal, a body posture signal, an activity level signal and a detachment status signal.

The method may further include wherein the second group of features associated with the ECG sample includes at least one of a ratio of abnormal beats to normal beats, a ratio of noise beats to non-noisy beats, ECG sample statistics, and beat/heart rate and variability statistics.

The method may further include wherein detected rhythm abnormalities include one or more of tachycardia, bradycardia, pause, atrial fibrillation, and ventricular tachycardia/ventricular fibrillation (VT/VF).

The method may further include wherein the one or more features associated with the ECG sample includes at least one of a ratio of abnormal beats to normal beats, a ratio of noise beats to non-noisy beats, ECG sample statistics, and beat/heart rate and variability statistics.

The method may further include wherein the ratio of abnormal beats to normal beats is greater than or equal to a first threshold to enable flagging the ECG sample for urgent review, and wherein the ratio of noise beats to non-noisy beats is less than or equal to a second threshold to enable flagging the ECG sample for urgent review, and wherein beat/heart rate and variability statistics monitored with respect to the ECG sample are within a range of physiological plausible levels to enable flagging the ECG sample for urgent review.

The method may further include wherein the first threshold is equal to or greater than 0.05 (5%), wherein the ratio of VT/VF beats to normal beats is greater than this threshold to enable flagging the ECG sample for urgent review, and wherein the second threshold is equal to or greater than 0.03 (3%), wherein the ratio of noise beats to non-noisy beats is less than this threshold to enable flagging the ECG sample for urgent review, and wherein the range of physiologically plausible beat/heart rate levels is defined as between twenty beats-per-minute (BPM) and three-hundred BPM.

In another embodiment, a system flags monitored ECG samples for urgent review by a human expert. In this embodiment, the system includes an adherent device that includes a plurality of electrodes and sensing circuitry for monitoring an electrocardiogram (ECG) signal of a patient to which the adherent device is affixed. The system further includes a processing module configured to receive the monitored ECG signal, wherein the processing module detects rhythm abnormalities in the patient based on the monitored ECG signal, collects an ECG sample associated with detected rhythm abnormalities, identifies one or more features associated with the ECG sample or monitored concurrently with collection of the ECG sample, and flags ECG samples for urgent review based on the one or more identified features. Flagged ECG samples are communicated to a human expert for review.

The system of the preceding paragraph can optionally include, additionally and/or alternatively any, one or more of the following features, configurations and/or additional components.

The processing module may discard ECG samples if it is determined from the one or more features that the ECG sample does not represent a physiological signal, wherein discarded ECG samples are not analyzed for flagging for urgent review.

The processing module may further include, when identifying one or more features associated with the ECG sample or monitored concurrently with the collection of the ECG sample, identifying a first group of features utilized to make determinations regarding whether the ECG sample represents a physiological signal and wherein the second group of features is utilized in the flagging step to determine whether the ECG sample should be flagged for urgent review, wherein a determination that the ECG sample does not represent a physiological signal results in the ECG sample being discarded.

The system may further include wherein the adherent device further includes one or more of an bioimpedance sensor, a respiration sensor, an accelerometer, and a detachment sensor, and wherein the first group of features comprises at least one of a bio-impedance signal, a respiration signal, a body posture signal, an activity level signal and a detachment status signal.

The system may further include wherein the second group of features associated with the ECG sample includes at least one of a ratio of abnormal beats to normal beats, a ratio of noise beats to non-noisy beats, ECG sample statistics, and beat/heart rate and variability statistics.

The system may further include wherein the processing module is distributed between the adherent device and a remote monitoring center.

The system may further include wherein the processing module detects rhythm abnormalities and collects corresponding ECG samples locally on the adherent device, wherein the collected ECG samples are communicated to the remote monitoring center, wherein flagging of ECG samples for urgent review is performed remotely at the remote monitoring center.

The system may further include wherein the one or more features identified by the processing module include at least one of a ratio of abnormal beats to normal beats, a ratio of noise beats to non-noisy beats, ECG sample statistics, beat/heart rate statistics, and detachment status of the adherent device.

The system may further include wherein the plurality of features are compared to threshold values to determine if the ECG sample should be flagged for urgent review by a human expert.

The system may further include wherein the processing module detects rhythm abnormalities that include one or more of tachycardia, bradycardia, pause, atrial fibrillation, and ventricular tachycardia/ventricular fibrillation (VT/VF).

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of flagging monitored ECG samples for urgent review by a human expert, the method comprising:
   continuously monitoring, using an adherent device having at least two electrodes and ECG circuitry, an electrocardiogram (ECG) signal of the patient;
   monitoring, using the adherent device, one or more physiological signals other than the ECG signal, including one or more of bio-impedance signal, respiration signal, body posture signal, and activity level;
   detecting, using a local processor module included on the adherent device, a rhythm abnormality in the patient based on the monitored ECG signal;
   storing, in a local memory located on the adherent device, an ECG sample associated with the detected rhythm abnormality;
   deriving, using the local processor module, one or more first features from the one or more monitored physiological signals, wherein the one or more first features are associated with the stored ECG sample;
   determining whether the ECG sample represents a physiological signal based on the one or more first features;
   discarding ECG samples that do not represent a physiological signal;
   communicating, using wireless communication circuitry located on the adherent device, ECG samples determined to represent a physiological signal to a remote monitoring center;
   deriving, at the remote monitoring center, one or more second features associated with the communicated ECG samples;
   flagging communicated ECG samples for urgent review based on the one or more second features; and
   placing flagged ECG samples in a prioritized queue at the remote monitoring center for out-of-order review by a human expert.

2. The method of claim 1, wherein the second group of features associated with the ECG sample includes at least one of a ratio of abnormal beats to normal beats, a ratio of noise beats to non-noisy beats, ECG sample statistics, and beat/heart rate and variability statistics.

3. The method of claim 2, wherein the ratio of abnormal beats to normal beats is greater than or equal to a first threshold to enable flagging the ECG sample for urgent review, and wherein the ratio of noise beats to non-noisy beats is less than or equal to a second threshold to enable flagging the ECG sample for urgent review, and wherein beat/heart rate and variability statistics monitored with respect to the ECG sample are within a range of physiological plausible levels to enable flagging the ECG sample for urgent review.

4. The method of claim 3, wherein the first threshold is equal to or greater than 0.05 (5%), wherein the ratio of VT/VF beats to normal beats is greater than this threshold to enable flagging the ECG sample for urgent review, and wherein the second threshold is equal to or greater than 0.03 (3%), wherein the ratio of noise beats to non-noisy beats is less than this threshold to enable flagging the ECG sample for urgent review, and wherein the range of physiologically plausible beat/heart rate levels is defined as between twenty beats-per-minute (BPM) and three-hundred BPM.

5. The method of claim 1, wherein detected rhythm abnormalities include one or more of tachycardia, bradycardia, pause, atrial fibrillation, and ventricular tachycardia/ventricular fibrillation (VT/VF).

6. A system for flagging monitored ECG samples for urgent review by a human expert, the system comprising:
an adherent device comprising:
    a plurality of electrodes;
    sensing circuitry coupled to the plurality of electrodes for monitoring an electrocardiogram (ECG) signal of a patient to which the adherent device is affixed;
    at least one of an accelerometer and bioimpedance circuitry configured to monitor one or more physiological signals other than the ECG signal, including one or more of a bio-impedance signal, a respiration signal, a body posture signal, and an activity level;
    a local processing module configured to receive the monitored ECG signal, wherein the processing module detects rhythm abnormalities in the patient based on the monitored ECG signal and stores an ECG sample associated with detected rhythm abnormalities to a local memory, wherein in response to a detected rhythm abnormality, the local processing module derives one or more first features from the one or more physiological signals and based on the one or more first features determines whether the ECG sample represents a physiological signal, wherein the ECG sample is discarded if determined to be a non-physiologic signal; and
    wireless communication circuitry configured to communicate ECG samples determined to represent a physiological signal; and
a remote monitoring center configured to receive ECG samples communicated from the adherent device, wherein the remote monitoring center derives one or more second features from the ECG samples and determines based on the derived second features whether the ECG sample should be flagged for urgent review, wherein flagged ECG samples are provided to a prioritized queue while non-flagged ECG samples are provided to a normal queue for human review.

7. The system of claim 6, wherein the second group of features associated with the ECG sample includes at least one of a ratio of abnormal beats to normal beats, a ratio of noise beats to non-noisy beats, ECG sample statistics, and beat/heart rate and variability statistics.

8. The system of claim 7, wherein the ratio of abnormal beats to normal beats is greater than or equal to a first threshold to enable flagging the ECG sample for urgent review, and wherein the ratio of noise beats to non-noisy beats is less than or equal to a second threshold to enable flagging the ECG sample for urgent review, and wherein beat/heart rate and variability statistics monitored with respect to the ECG sample are within a range of physiological plausible levels to enable flagging the ECG sample for urgent review.

9. The system of claim 8, wherein the first threshold is equal to or greater than 0.05 (5%), wherein the ratio of VT/VF beats to normal beats is greater than this threshold to enable flagging the ECG sample for urgent review, and wherein the second threshold is equal to or greater than 0.03 (3%), wherein the ratio of noise beats to non-noisy beats is less than this threshold to enable flagging the ECG sample for urgent review, and wherein the range of physiologically plausible beat/heart rate levels is defined as between twenty beats-per-minute (BPM) and three-hundred BPM.

10. The system of claim 6, wherein the one or more features are compared to threshold values to determine if the ECG sample should be flagged for urgent review by a human expert.

11. The system of claim 6, wherein the local processing module detects rhythm abnormalities that include one or more of tachycardia, bradycardia, pause, atrial fibrillation, and ventricular tachycardia/ventricular fibrillation (VT/VF).

* * * * *